(12) United States Patent
Bent (10) Patent No.: US 7,284,855 B2
(45) Date of Patent: Oct. 23, 2007

(54) SPORTS SUNGLASSES

(76) Inventor: David Bent, 4904 Seashore Dr., Newport Beach, CA (US) 92663

( * ) Notice: Subject to any disclaimer, the term of this patent is extended or adjusted under 35 U.S.C. 154(b) by 0 days.

(21) Appl. No.: 11/210,476

(22) Filed: Aug. 24, 2005

(65) Prior Publication Data

US 2005/0280773 A1  Dec. 22, 2005

(51) Int. Cl.
*G02C 3/00* (2006.01)
(52) U.S. Cl. ........................ 351/156; 351/157
(58) Field of Classification Search ............... 351/156, 351/157, 111, 41, 158, 123, 121, 122, 114
See application file for complete search history.

(56) References Cited

U.S. PATENT DOCUMENTS 4,978,210 A * 12/1990 Lundbeck .................. 351/157

5,235,355 A * 8/1993 May ........................... 351/123
6,533,413 B2 * 3/2003 Wright et al. ............... 351/156

* cited by examiner

*Primary Examiner*—Hung Xuan Dang
(74) *Attorney, Agent, or Firm*—Norman E. Carte; MacPherson Kwok Chen & Heid LLP

(57) ABSTRACT

Glasses for use in sports activities and the like have a frame, at least one lens formed to the frame, and a strap formed to the frame which is configured to inhibit the glasses from falling off of a wearer. A leash is formed to the strap and a collar formed to the leash. The strap, leash, collar or other component of the present invention may optionally be sufficiently buoyant so as to float the glasses in water. A breakaway clip releases the collar from a wearer if the glasses, strap, leash, or collar get caught.

15 Claims, 4 Drawing Sheets

SPORTS SUNGLASSES

PRIORITY CLAIM

This patent application claims the benefit of the priority date of U.S. patent application Ser. No. 10/771,699, filed on Feb. 3, 2004 and entitled SPORTS SUNGLASSES, which claims the benefit of the priority date of U.S. Provisional Patent Application Ser. No. 60/445,867, filed on Feb. 6, 2003 and entitled SURF SHADES-SUNGLASSES FOR USE IN AND ON THE WATER pursuant to 35 USC 119. The entire contents of these two patent applications are hereby expressly incorporated by reference.

FIELD OF THE INVENTION

The present invention relates generally to sporting goods. The present invention relates more particularly to glasses, sunglasses, and the like that are especially suitable for use in sports, particularly water sports, wherein a strap is configured to attach the glasses to a user and wherein a breakaway clip enhances safety by allowing the glasses to detach from the user if the glasses get caught (such as on an underwater object).

BACKGROUND OF THE INVENTION

Sunglasses for mitigating bright light and glare are well known. Sunglasses are frequently worn by people who are engaging in outdoor sports activities. For example, snow skiers, bicyclists, and boaters frequently wear sunglasses.

Glare frequently interferes with sports enthusiasts' ability to perform. Glare is particularly problematic in water sports activities, where sunlight is commonly reflected off of the water and into a person's eyes. Glare not only inhibits desired performance, but may also contribute to accidents, such as when it prevents a person from seeing adequately. It is easy to appreciate the importance of seeing nearby swimmers when boating, for example.

It can also be desirable to wear sunglasses so as to mitigate the health risks associated with overexposure of the eyes to sunlight, particularly the ultraviolet (UV) component thereof. It is well known that overexposure to ultraviolet radiation from the sun can cause or exacerbate cataracts, for example.

However, although contemporary sunglasses have proven generally suitable for their intended purposes, they possess inherent deficiencies that detract from their overall effectiveness and desirability. For example, the use of sunglasses in water sports activities presents problems with their potential loss if they inadvertently come off of the wearer. This is particularly true if the sunglasses sink into the water.

The potential loss of sunglasses during water sports activities is troublesome because sunglasses can be expensive and because participation in water sports activities such as surfing, windsurfing, and water skiing provides ample opportunity for the sunglasses to be knocked off of the wearer. The loss of sunglasses during any sporting activity can be especially troublesome if they are prescription sunglasses and cannot be immediately replaced.

In an attempt to mitigate the problem of having sunglasses inadvertently come off during water sports activities, companies such as Croakies of Jackson Hole, Wyo. have developed straps which attach to sunglasses and which, to some degree, secure the sunglasses to a wearer and help prevent their loss.

Croakies also provides a product having a buoyant strap, so that the sunglass will float if they do inadvertently come off of a wearer during a water sports activity. This way, the sunglasses can generally be easily recovered.

However, such contemporary straps, even if buoyant, do not always prevent the loss of sunglass that inadvertently come off during a water sports activity. Sometimes, the wearer may travel a considerable distance after the sunglasses come off, thus making finding them difficult even if they are floating.

It is easy to appreciate that by the time a surfer, water skier or boater manages to come to a stop after losing a pair of sunglasses while traveling fast on the water, that person may be far from the location where the sunglasses were lost. Indeed, the wearer may not even be able to pinpoint the location where the sunglasses were lost. Therefore, sometimes the sunglasses cannot be retrieved even if they are attached to a floating strap.

Because they may easily become lost, sunglasses are not worn by water sports enthusiasts as frequently as they may desire. Thus, water sports enthusiasts may sometimes undesirably forego the benefits of wearing sunglasses.

Another problem associated with the wearing of contemporary sunglasses, at least when the sunglasses are attached to the user with a strap, is that the sunglasses, the strap, or some associated item, could get caught on something that could endanger the safety of the wearer.

For example, the sunglasses could get caught on underwater coral. If the wearer could not quickly get free, then the wearer's safety could be seriously jeopardized. That is, the wearer could drown if the wearer could not get to the surface promptly.

As such, although the prior art has recognized, to a limited extent, the problem of losing sunglasses during water sports and similar activities and the problem of facilitating quick detachment of the sunglasses if the get caught, the proposed solutions have, to date, been ineffective in providing a satisfactory remedy. Therefore, it is desirable to provide glasses, such as sunglasses, which are not likely to be lost during sports activities and which can easily be detached from a wearer if the sunglasses or some item attached to the sunglasses (such as a strap or leash) gets caught.

BRIEF SUMMARY OF THE INVENTION

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

The present invention specifically addresses and alleviates the above mentioned deficiencies associated with the prior art. More particularly, the present invention comprises glasses, such as sunglasses, for use in sports activities. According to one aspect, the glasses comprise a frame, at least one lens formed to the frame, and a strap formed to the frame. The strap is configured to inhibit the glasses from falling off of a wearer, such as during vigorous sports activities. Thus, the strap inhibits undesirable loss of the glasses.

A leash is optionally formed to the strap and a collar is formed to the leash. The leash and collar cooperate to further inhibit undesirable loss of the glasses. That is, if the strap fails to keep the glasses on a user's head, the strap and the collar cooperate to keep the glasses proximate the user so that they do not become lost.

According to one aspect, the frame comprises a flexible frame. For example, the frame may be comprised of a resilient polymer material, natural rubber, silicone rubber, or any other desired flexible material.

The lenses may comprise either sunglass lenses or non-sunglass lenses Thus, the glasses may be clear, tinted, or photogray (darken in the presence of light). The lenses may comprise either prescription lenses or non-prescription lenses.

The strap, the leash, and the collar may comprise neoprene, natural rubber, synthetic rubber such as silicone rubber, or any other flexible material. The strap, the leash, and/or the collar may optionally be buoyant so as to float a pair of glasses attached to the leash assembly. Thus, if the leash and collar fail to keep the glasses proximate the wearer, then they will preferable float, so as to facilitate their being more easily found.

The collar preferably comprises a release. The release allows the collar to be placed around a wearer's neck. The release also allows the collar to come off of the wearer if the leash assembly and/or glasses become caught. For example, if a surfer wipes out and the leash assembly becomes caught on some underwater coral, then the release opens and allows the collar to come off of the wearer, so that the wearer is less likely to drown or otherwise sustain injury.

The release may comprise a Velcro release, for example. Alternatively, the release may comprises a snap or other mechanical device that pulls apart, breaks, or otherwise allows the collar to open when the leash is pulled with sufficient force.

Optionally, the collar is formed of an expandable or stretchable material, such that it can be pulled over the head to be worn. As a further alternative, the collar may be formed of an expandable or stretchable material, such as rubber, and configured such that it breaks if pulled upon with sufficient force. Thus, the collar may be stretched so as to be pulled down around the head and onto the neck in order to be worn. It may be removed in a similar fashion during normal use. However, if the glasses or leash assembly become caught underwater, the collar or the leash are configured so as to break and thereby free the wearer. This may be accomplished by providing a weak point in the collar and/or the leash.

The strap may be either permanently or removably attached to the frame. Thus, the strap may attach to the frame of a pair of glasses by sliding over the earpieces thereof, in the fashion that Croakies are installed upon glasses. Alternatively, the strap may be permanently attached to the ear pieces, or earpiece stubs or other portions of the glasses such as by adhesive bonding, ultrasonic welding, the use of mechanical fasteners, or by forming the strap integrally with respect to the frame.

The glasses may comprise earpieces, like contemporary glasses. Alternatively, the glasses may comprise earpiece stubs or no earpieces or the like whatsoever. The earpiece is that portion of the glasses which extends toward and partially wraps around the ear. An earpiece stub is similar, but lacks that portion which wraps around the ear and serves as an attachment point for the strap.

The leash may attach to the strap and the collar by any desired method. For example, the leash may have a loop formed in one or both ends thereof for receiving and attaching to the strap and/or the collar. Alternatively, the leash may be formed integrally with the strap and/or the collar.

A breakaway clip can be used to facilitate detachment of the glasses from a wearer in the event that the glasses, strap, lease, collar, or other item get caught. Thus, the glasses can be detached from a wearer if the glasses, for example, get caught on coral or some other object underwater.

The breakaway clip can be attached to the collar so as to facilitate detachment of the collar from the wearer. The breakaway clip can alternatively be attached to the leash or strap.

The breakaway clip can be configured so as to pull apart with less than ten pounds of force. The breakaway clip can be configured so as to pull apart with a different amount of force.

The strap, leash, and/or collar can comprises ¾ inch wide stretchable neoprene that is folded approximately in half and optionally sewn around a ⅜ inch diameter buoyant foam tube. Those skilled in the art will appreciate that other materials are likewise suitable. The strap, or some combination of the strap, leash and collar, can have sufficient buoyancy so as to float when attached to the frame and lenses.

These, as well as other advantages of the present invention, will be more apparent from the following description and drawings. It is understood that changes in the specific structure shown and described may be made within the scope of the claims, without departing from the spirit of the invention.

BRIEF DESCRIPTION OF THE DRAWINGS

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

Thus, the detailed description set forth below in connection with the appended drawings is intended as a description of the presently preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions may be accomplished by different embodiments that are also intended to be encompassed within the spirit of the invention.

Figure 1:
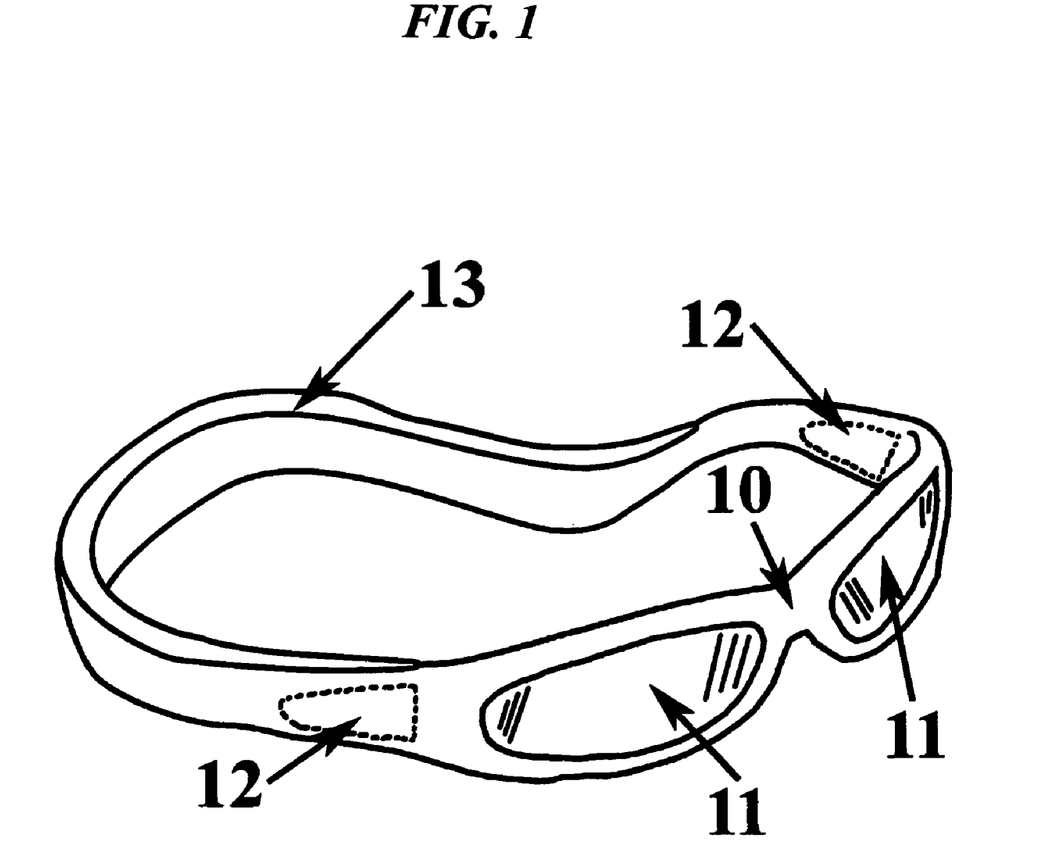
FIG. 1 is a perspective view of an exemplary embodiment of the sports glasses of the present invention showing a buoyant strap formed to earpiece stubs of a flexible and resilient frame.
Figure 2:
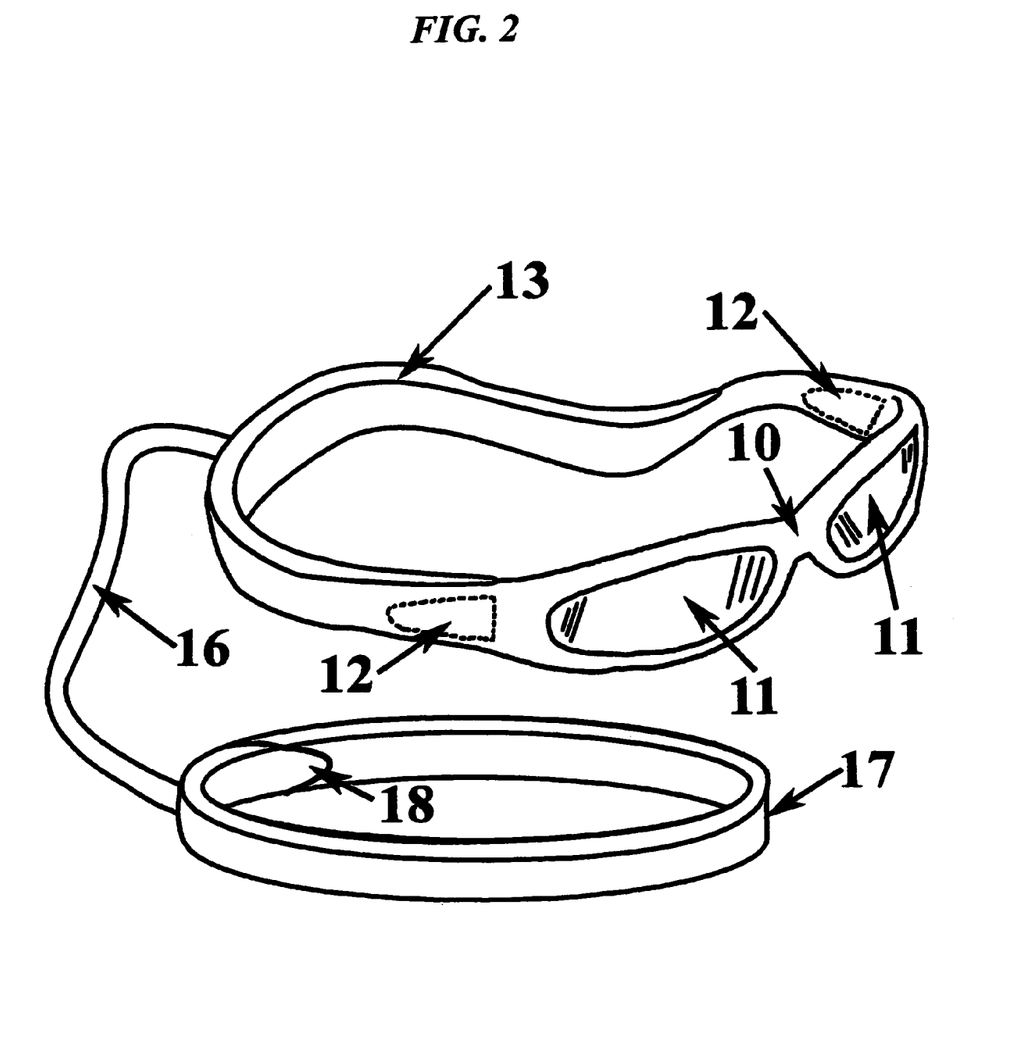
FIG. 2 is a perspective view of another exemplary embodiment of the sports glasses of the present invention showing a leash and collar assembly formed to the buoyant strap.
Figure 3:
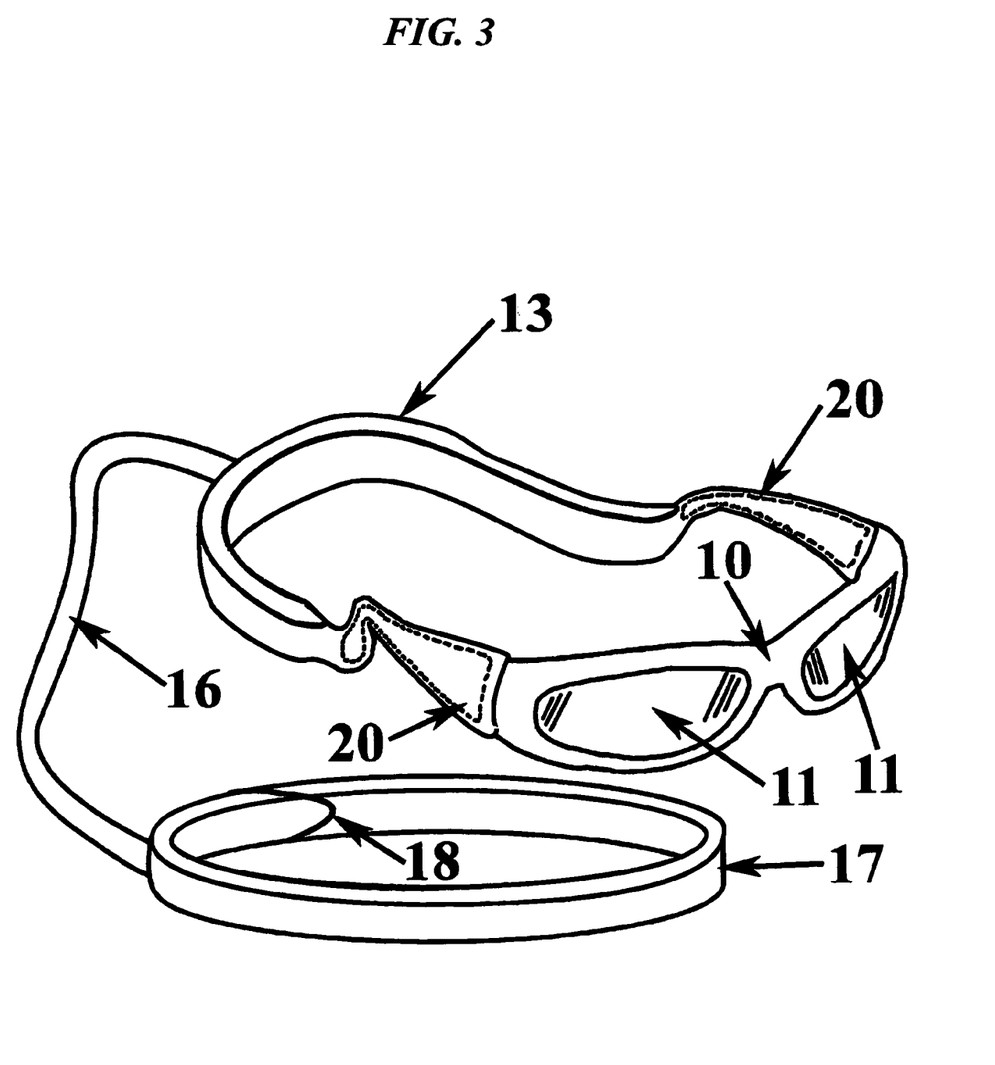
FIG. 3 is a perspective view of yet another exemplary embodiment of the sports glasses of the present invention showing a leash and collar assembly formed to a buoyant strap, which in turn is formed to earpieces of a contemporary pair of sunglasses.

The present invention is illustrated in FIGS. 1-3, which depict presently preferred embodiments thereof. Although the invention discussed with reference to these figures is a pair of sunglasses, those skilled in the art will appreciate that the present invention is applicable to other types of glasses, including non-sunglasses, prescription glasses, goggles (such as those commonly used for swimming, snorkeling, scuba diving, water skiing and snow skiing), as well as other types of eyewear. Thus, discussion of the glasses herein as sunglasses is by way of example only, and not by way of limitation.

Referring now to FIG. 1, one exemplary embodiment of the present invention comprises a flexible and resilient frame 10, which may be formed of natural rubber, synthetic rubber such as silicone rubber, a resilient polymer material, or any other desired material. The frame 10 is thus preferably soft, lightweight and pliable. Thus, the frame 10 will easily deform and return to its normal shape after an impact or other bending thereof.

Lenses 11 are formed to the frame 10. The lenses may be either sunglass lenses or prescription lenses, as discussed above. The lenses 11 may be either permanently or removably attached to the frame 10 according to well known principles.

Either a pair of lenses or a single lens may be used. For example, a snorkeling or scuba mask made according to the present invention may have a single lens.

By way of contrast, the present invention may alternatively comprise more than two lenses. For example, two lenses for each eye (giving a total of four lenses), may be provided for some applications, such as ski or scuba goggles.

Earpiece stubs 12 extend rearwardly from the frame 10 toward the ears. A strap 13 attaches either permanently or removably to the earpiece stubs 12. Optionally, the earpiece stubs 12 may be hinged to the frame 10. Preferably, at least one end of the strap 13 attaches removably to the associated earpiece stub 12, such that the strap 13 can easily be detached from the frame 10 and cut to a desired length by the user to facilitate comfortable and secure wearing of the sports glasses of the present invention.

The strap 13 may be attached to the earpiece stubs 12 by a stretched fit thereover, in the fashion that Croakies are attached to a contemporary pair of glasses. That is, the strap 13 may be tubular or hollow in construction, such that the earpiece stubs 12 (or the earpieces 20 of FIG. 3) can be pushed into and frictionally engage the strap 13. Alternatively, the strap 13 may be adhesively bonded, ultrasonically welded, or attached to the earpiece stub 12 by mechanical fasteners or by any other desired method.

The strap 13 may optionally be integrally formed with the frame 10. Thus, the strap 13 may be formed via the same process as the frame 10 and may be formed from the same material.

Preferably, the strap 13 is formed of a buoyant material which has sufficient buoyancy that it remains afloat when attached to a pair of glasses. The strap 13 may, for example, be formed of neoprene so as to provide the desired buoyancy. Alternatively, sufficient buoyancy to float the glasses may be provided by adding buoyant material to the strap, or to any other component of the present invention.

Referring now to FIG. 2, an optional leash assembly, which may be formed to the strap 13, comprises leash 16 and collar 17. The leash 16 and the collar 17 are preferably formed of the same flexible material, such as neoprene. Alternatively, the leash 16 and the collar 17 may be formed of different materials. For example, the leash 16 may be formed of nylon cord and the collar 17 may be formed of rubber.

The collar 17 preferably comprises a release 18. The release preferably comprises a Velcro release wherein two pieces of Velcro adhere to one another to connect two ends of the collar 17 to one another in a fashion similar to a belt buckle attaching two ends of a belt to one another. Alternatively, the release may comprise a snap or a weak breakable portion of the collar 13. The release 18 is preferably formed near where the leash 16 attaches to the collar 17, such that pulling the leash 16 tends to pull the release 18 open. Thus, pulling on the least 16 will cause the release 18 to open and the collar 17 to come off.

The use of a release is particularly advantageous in the event that the strap, lease, or glasses gets caught on something underwater, as discussed above.

Referring now to FIG. 3, a leash assembly comprising a leash 16 and a collar 17 may be provided as an aftermarket product for use with standard contemporary sunglasses or the like. The use of such a leash assembly facilitates the retrofitting of a standard contemporary pair of sunglasses, so as to obtain at least some of the desired characteristics and functionality of the present invention. That is, such retrofitting provides a way to mitigate the undesirable loss of the contemporary pair of sunglasses by providing a leash 16 and a collar 17 which keep the sunglasses with the wearer if they come off of the wearer and by optionally providing buoyancy to float the sunglasses if the become separated from the wearer.

Contemporary glasses have earpieces 20 that may be either hinged or not hinged to the frame 10.

In use, the sports glasses of the present invention shown in FIG. 1 are simply slipped on by passing the strap 13 behind the wearer's head. In the event of an accident, such as a surfboard hitting a surfer in the face, the flexible frame 10 is substantially less likely to cause trauma as compared to the rigid frame of a pair of contemporary sunglasses.

In use, the sports glasses of the present invention shown in FIG. 2 are generally worn by first putting on the collar 17. This may be accomplished, for example, by opening the release 18, placing the collar 17 about the wearer's neck, and closing the release 18. Alternatively, the collar 13 may comprise a stretchable material, such that the collar 13 can simply be pulled over the wearer's head. The sunglasses are then put on by positioning the strap 13 behind the wearer's head as described above.

In use, the sports glasses of the present invention shown in FIG. 3 are put on in a fashion similar to those shown in FIG. 2 and discussed above. However, since the leash assembly for the glasses shown in FIG. 3 is an aftermarket product, it must be installed upon the glasses before they are worn.

The exemplary leash assembly of FIG. 3 is installed upon the glasses by pushing the ends of the strap 13 over the earpieces of the glasses in the fashion that Croakies are installed upon glasses.

Thus, if the sunglasses of either FIG. 2 or FIG. 3 come off of the wearer's head, such as during a surfing wipeout or duck diving, the wearer can easily reposition the sunglasses upon the head.

If any part of the sun sunglasses and/or leash assembly of either FIG. 2 or FIG. 3 get caught on an underwater structure (such as coral), on the surfboard, or on any other item, then the release 18 opens as the wearer pulls away from the item and the collar 17 comes off of the wearer, such that the wearer is less likely to become undesirably trapped.

If the sunglasses of either FIG. 1 or FIG. 2, which both have a buoyant strap 13, come off during use, then they will generally float so that then can easily be located.

Preferably, the lenses of the glasses are formed of scratch resistant, ultraviolet (UV) protection providing, anti-fog, and anti-water spot material. For sunglasses, polarized lenses are preferred.

The present invention may find application in a wide variety of water sports, including surfing, wind surfing, water skiing, wake boarding, skim boarding, kite surfing, jet skiing, boating, white water rafting, snorkeling, scuba diving and others. Indeed, the present invention is not limited to water sports and may application in a wide variety of non-water sports, such as snow skiing, snow boarding, foul or cold weather use, sand storm use, sky diving and others.

If desired, the lease assembly of FIG. 2 and FIG. 3 can be removed and the sunglasses used in the manner of those of FIG. 1.

The strap 13, the leash 16 and the collar 17 can be black, or can be of a color and/or pattern that will increase their visibility, such as on the land, on snow, on sand, on the surface of water, and/or underwater.

Any desired portion of the present invention, including the frame 10, the strap 13, the lease 16, and/or the collar 17 may be made buoyant, so as to enhance the floatability thereof. Further, floats or buoyant members may be added to any desired portion of the sunglasses. Alternatively, any portion of the sunglasses may be made so as to be non-buoyant, as desired.

Figure 4:
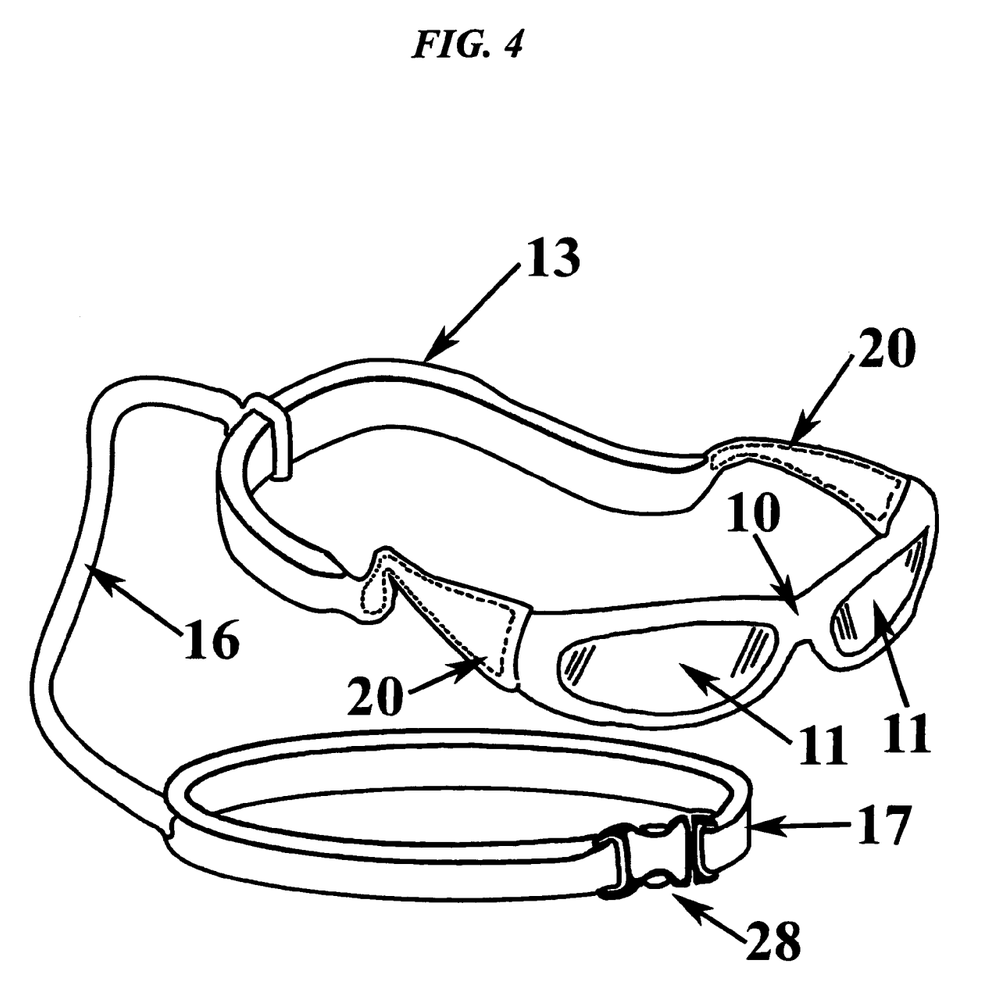
FIG. 4 is a perspective view of yet another exemplary embodiment of the sports glasses of the present invention showing a breakaway clip attached to the collar thereof.

Referring now to FIG. 4, a breakaway clip 28 has been added to collar 17. The breakaway clip 18 is configured to automatically release if the frame 10, strap 13, leash 16 and/or collar 17 gets caught or entangled upon something. Thus, the breakaway clip 28 is configured to release if one of these items gets caught upon underwater coral, for example. By releasing, the breakaway clip detaches the collar 17 from the wearer so as to mitigate the likelihood of the wearer being trapped (such as being trapped underwater, for example).

A breakaway clip can alternatively or additionally be attached to other portions of the present invention. For example, a breakaway clip can be attached to the strap 13 and/or the leash 16. Such attachment can be similar to attachment of the breakaway clip 18 to the collar 17. Thus, the strap 13 can open or release and/or the leash 16 can pull apart.

The breakaway clip 28 can comprise a breakaway clip similar to those used on cat collars to prevent cats from getting caught. Such breakaway clips are configured to release and thus detach the collar from a cat if the collar gets caught. Such detachment of the collar may prevent the cat from being strangled. One example of a suitable breakaway clip is part number 7308/7262 provided by John Howard Company, of Chino, Calif. This breakaway clip has a width of ⅜ inch, is formed of acetal, and comprises male and female portions that releasably attach to one another. Openings in the male and female portions facilitate their attachment to the collar 17, such as via looping the ends of the collar through the openings and sewing the looped portions of the collar.

The breakaway clip can be configured to release when pulled with a force of approximately ten pounds or less. The amount of force can depend upon the application (surfing, skiing, skydiving, etc.), the body weight of the wearer, and/or the preferences of the wearer. The force needed to release the breakaway clip can be adjustable or multiple clips can be provided (each having a different release force) and then the desired clip can be used.

Thus, the present invention provides sports glasses, such as sunglasses, which are less likely to be lost than contemporary glasses when worn during vigorous sports activities and also which release the wearer if they get caught, so as not to endanger the wearer.

The strap 13 can comprise stretchable neoprene, such as approximately ¾ inch wide neoprene that is approximately 2 millimeters thick. The strap 13 can be formed by folding the neoprene generally in half along its length, such that the neoprene is folded around buoyant foam, such as a ⅜ inch buoyant foam tube. The strap 13 can be sewn so as to capture the foam tube therein. The strap 13 can have a length that is suitable for use with a particular size of wearer's head.

For example, the strap can be approximately 10 inches in length. The strap can be substantially longer, so as to facilitate attachment thereof to glasses. For example, the strap can have a total length of approximately 19 inches with 10 inches of buoyant foam captured beneath the folded over portions thereof. At each end of the strap, approximately 3 to 4 inches thereof receive the earpieces of frame 10. The edges of the strap are sewn so as to form bores that tightly hold the earpieces, much in the fashion of Croakies. Optionally, the strap can extend past the earpieces toward hinges of the frame 10, and can extend right up to the hinges.

The strap can be attached to the frame 10 by any desired method. For example, the ends of the strap 13 can be pushed over the earpieces 20 of the frame 10. The ends of strap 13 can be pushed over the earpieces 20 until strap 20 completely covers earpieces 20 and thus terminates in the temple region of frame 10. Openings in the ends of the strap 13 can be sized so as to receive and securely hold the earpieces 20.

The leash 16 can similarly be ¾ inch, 2 millimeter thick neoprene that is folded in half and sewn together. The leash 16 can be approximately 4 to 5 inches long. Optionally, the neoprene leash 16 can also be sewn about buoyant foam tubing. Leash 16 can be attached to strap 13 by forming (such as via sewing) a loop in one end of leash 16 and inserting strap 13 through the loop. The loop can utilize approximately 1 inch of the strap. Leash 16 can also sewn to strap 13. Leash 13 can be attached to collar 17 in a similar fashion (via a loop or via sewing). The leash 13 can be sewn to the back of collar 17, which can be that portion of collar 17 that is opposite (approximately 180 degrees) from breakaway clip 18.

The collar 17 can similarly be formed of ¾ inch, 2 millimeter thick neoprene that is folded in half and sewn together. The two portions of breakaway clip can be sewn to the two ends of collar 17. The collar 17 can be approximately 18 to 20 inches long (in circumference), for example. Generally, the length of collar 17 will be that length that can be comfortably worn, while being too small to slip over the head.

Thus, according to at least one embodiment, the present invention can be formed from three pieces or strips of 2 millimeter, ¾ inch wide neoprene, wherein each pieces is folded in half along the length thereof and sewn so as to define three ⅜ inch wide elongate strips. The strap 13, the leash 16, and the collar 17 can all be buoyant. Alternatively, only one or two of these three items can be buoyant. The important thing is that some part of the strap, leash, and collar assembly or that some combination of parts be sufficient buoyant so as to prevent the assembly and the glasses from sinking if they come off of the wearer.

It is understood that the exemplary embodiments of the sports glasses described herein and shown in the drawings represents only presently preferred embodiments of the invention. Indeed, various modifications and additions may be made to such embodiments without departing from the spirit and scope of the invention.

For example, the leash 16 may be made of either a stretchable material such as elastic or may be made of a non-stretchable material such as nylon cord. Further, the strap 13 may similarly be made of a stretchable material such as neoprene, rubber, or elastic, or may alternatively be made of a non-stretchable material such as nylon, cloth, or plastic.

Thus, these and other modifications and additions may be obvious to those skilled in the art and may be implemented to adapt the present invention for use in a variety of different applications.

The invention claimed is:

1. Glasses for use in sports activities, the glasses comprising:
   a frame;
   at least one lens formed to the frame;
   a strap formed to the frame and configured to inhibit the glasses from falling off of a wearer;
   a leash formed to the strap;
   a collar formed to the leash;
   a breakaway clip formed to the collar, the breakaway clip configured so as to facilitate detachment of the collar from the wearer, the breakaway clip comprising:
   a male portion;
   a female portion configured to receive the male portion;
   wherein the male portion and the female portion releasably attach to one another; and
   wherein the male portion and the female portion release from one another when pulled with a force of less than ten pounds.

2. The glasses as recited in claim 1, wherein the collar comprises neoprene that is folded around a buoyant foam tube.

3. The glasses as recited in claim 1, wherein the collar comprises ¾ inch wide stretchable neoprene that is folded approximately in half and sewn around an approximately ⅜ inch diameter buoyant foam tube.

4. The glasses as recited in claim 1, wherein the collar comprises ¾ inch wide stretchable neoprene that is folded approximately in half and sewn around an approximately ⅜ inch diameter buoyant foam tube, wherein the strap has sufficient buoyancy so as to float when attached to the frame and lenses.

5. The glasses as recited in claim 1, wherein the collar is formed of stretchable neoprene.

6. The glasses as recited in claim 1, wherein the strap is attached to the frame by inserting ends of the strap over the temples of sunglasses.

7. The glasses as recited in claim 1, wherein the frame comprises a resilient polymer.

8. The glasses as recited in claim 1, wherein the lenses comprise sunglass lenses.

9. The glasses as recited in claim 1, wherein the lenses comprise prescription lenses.

10. The glasses as recited in claim 1, wherein at least one of the strap, the leash, and the collar comprise neoprene.

11. The glasses as recited in claim 1, wherein at least one of the swap, the leash, and the collar is sufficiently buoyant so as to float a pair of glasses.

12. The glasses as recited in claim 1, wherein the strap is removably attached to the frame.

13. The glasses as recited in claim 1, further comprising two earpieces formed to the frame via which the strap is formed to the frame.

14. A leash assembly for glasses, the leash assembly comprising:
   a leash configured to attach to glasses;
   a collar formed to the leash; and
   a breakaway clip configured so as to facilitate detachment of the collar from the wearer, the breakaway clip comprising:
   a male portion;
   a female portion configured to receive the male portion;

wherein the male portion and the female portion releasably attach to one another; and wherein the male portion and the female portion release from one another when pulled with a force of less than ten pounds.

15. The leash assembly as recited in claim 14, wherein the collar comprises neoprene that is folded around a buoyant foam tube.

* * * * *